US00PP08874P

United States Patent [19]

Tvrtkovic-Sahin et al.

[11] Patent Number: Plant 8,874

[45] Date of Patent: Aug. 30, 1994

[54] ASTER PLANT NAMED DARK BLUE BUTTERFLY

[75] Inventors: Zelimir K. Tvrtkovic-Sahin, Alphen aan den Rijn; Petrus J. Akerboom, Ter Aar, both of Netherlands

[73] Assignee: DeNachtvlinder B.V., Paradijsweg, Netherlands

[21] Appl. No.: 7,235

[22] Filed: Jan. 21, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A distinct cultivar of aster plant named Dark Blue Butterfly, characterized by its cupped capitulum form; daisy capitulum type; dark violet-blue ray floret color; diameter across face of capitulum of 27 to 30 mm at maturity; strong, well branched flower stems; dark green leaves, and many capitula per inflorescence on short pedicels.

2 Drawing Sheets

The present invention comprises a new and distinct cultivar of Aster plant, hereinafter referred to by the cultivar name Dark Blue Butterfly.

Dark Blue Butterfly is a product of a planned breeding program which had the objective of creating new perennial Aster cultivars for year-round commercial production having well branched flower stems, good flower size, blue color, good flower form, and excellent lasting quality of the cut flowers. Such traits in combination were not present or needed improvement in previously available commercial cultivars.

Dark Blue Butterfly was originated from a hybridization made by the inventors K. Sahin and P. Akerboom in a controlled breeding program in Ter Aar, The Netherlands, in 1984. The female parent of Dark Blue Butterfly was an unnamed *Aster pringlei* seedling. The male parent was an unnamed *Aster novi-belgii* seedling. Each of the parent plants was a proprietary plant which had been maintained for breeding purposes only, and which had not been released by the inventors.

Dark Blue Butterfly was discovered and selected as one flowering plant within the progeny of the stated parentage by the inventors K. Sahin and P. Akerboom on Sep. 7, 1985 in a controlled environment in Ter Aar, and identified as seedling No. 84/893 dark blue.

The first act of asexual reproduction of Dark Blue Butterfly was accomplished when vegetative cuttings were taken from the initial selection in November 1985 in a controlled environment in Ter Aar, by a technician working under formulations established and supervised by K. Sahin and P. Akerboom.

Horticultural examination of selected units initiated in 1985 and 1986 has demonstrated that the unique combination of characteristics as herein disclosed for Dark Blue Butterfly are firmly fixed and are retained through successive generations of asexual reproduction.

Dark Blue Butterfly has not been observed under all possible environmental conditions. The phenotype may vary significantly with variations in environment such as temperature, light intensity and daylength, without, however, any variation in the genotype.

The following observations, measurements and comparisons describe plants grown in Ter Aar under greenhouse conditions which approximate those generally used in commercial greenhouse practice in The Netherlands.

The following traits have been repeatedly observed and are determined to be basic characteristics of Dark Blue Butterfly, which, in combination, distinguish this Aster as a new and distinct cultivar:

1. Cupped capitulum form.
2. Daisy capitulum type.
3. Dark violet-blue ray floret color.
4. Diameter across face of capitulum of 20 to 30 mm at maturity.
5. Strong, well branched flower stems.
6. Many capitula per inflorescence on short pedicels.
7. Dark green foliage.
8. Can be grown as a garden perennial or as a forced greenhouse cultivar. When forced, it will flower as many as three times a year.

In the accompanying color photograph drawings, the photograph on sheet 1 comprises a front view of a typical plant of Dark Blue Butterfly in bloom and bud.

The photograph on sheet 2 comprises a closeup view showing the flowers in much greater detail. The flowers are not as dark violet-blue as the true flower color value noted accurately below.

Of the commercial cultivars known to the inventor, the most similar to Dark Blue Butterfly is the cultivar Blue Butterfly, disclosed in U.S. Plant Pat. No. 7,399. Dark Blue Butterfly is a sibling of Blue Butterfly, both being in the progeny from the same cross. Dark Blue Butterfly is generally similar to Blue Butterfly except for flower and foliage color. Dark Blue Butterfly has a much darker violet-blue flower color (RHS 90A vs. RHS 92B for Blue Butterfly) and much darker leaves (RHS 139A vs. RHS 137A for Blue Buttterfly).

In the following description color references are made to the Royal Horitcultural Society Colour Chart. The color values were determined at Alphen aan den Rijn, The Netherlands.

Classification:

*Botanical.*—*Aster pringlei* × *novi-belgii* cv Dark Blue Butterfly.

*Commercial.*—Small daisy-like spray Aster, greenhouse or garden perennial.

INFLORESCENCE

A. Capitulum:

*Form.*—Cupped.

*Type.*—Daisy.

*Diameter across face.*—27–30 mm.

*Arrangement.*—Raceme inflorescence each branch.

*Flower production.*—Flowers to a degree similar to the sibling Blue Butterfly.

B. Corolla of ray florets:

*Color (upper surface).*—Closest to 90A.

*Color (under surface).*—Closest to 90B-C.

*Shape of floret.*—Narrow, oblong. Apex reflexing.

*Size of floret.*—10–12 mm long × 2–2.6 mm wide.

*Number of ray florets.*—27–29.

C. Corolla of disc florets:

*Color (mature).*—Closest to 1C-D.

*Color* (immature).—Closest to 1C-D.

*Diameter of disc.*—7–8 mm.

D. Reproductive organs:

*Androecium.*—Present on disc florets only; no pollen.

*Gynoecium.*—Present on both ray and disc florets.

*Fertility.*—The new cultivar is fertile and has been used in breeding as a female.

PLANT

A. General appearance:

*Height.*—Medium to tall, depending on light conditions. Under continuous long days it can grow up to 2 meters tall; heavy branching. Growth habit is vigorous.

The shape of the plant and the stems produced by this plant are typical of those of the parent species. The stems of this plant are well adapted for cut flower production, having sufficient strength without being too brittle.

B. Foliage:

*Color.*—139A.

*Shape.*—Very narrowly oblanceolate and linear, with occasional downward reflexing at the tip.

*Size.*—140–160 mm long × 12–13 mm wide.

*Margin.*—Entire.

*Arrangement.*—Alternate, with angle acute.

We claim:

1. A new and distinct Aster plant named Dark Blue Butterfly, as described and illustrated.

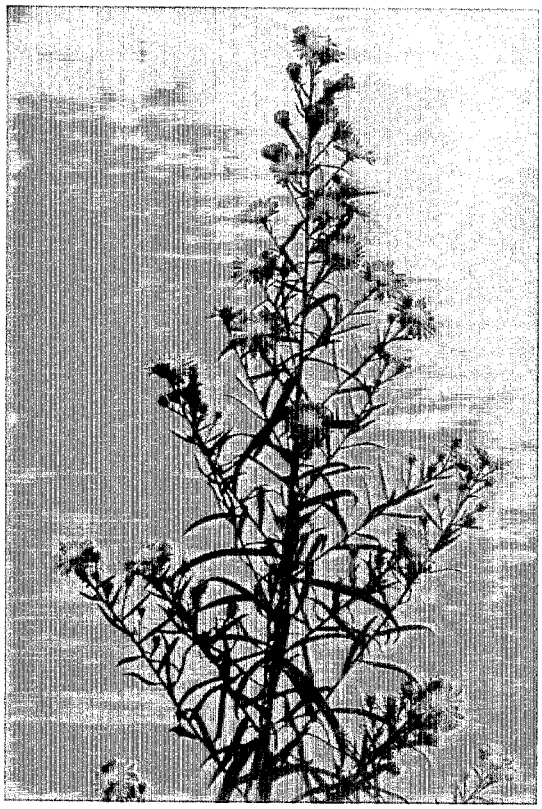

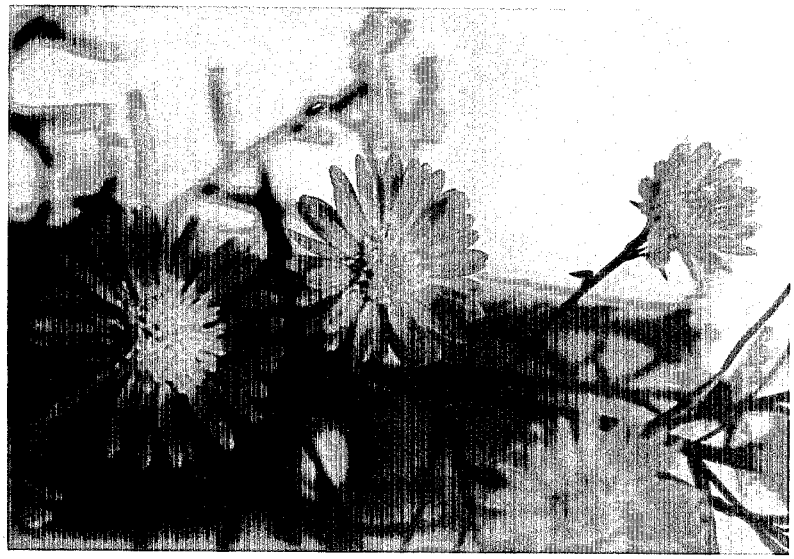

* * * * *